(12) United States Patent
Kralik (10) Patent No.: US 7,010,350 B2
(45) Date of Patent: Mar. 7, 2006

(54) TEMPORARY BIVENTRICULAR PACING OF HEART AFTER HEART SURGERY

(76) Inventor: Michael R. Kralik, 2746 Heritage Ave., NW., Canton, OH (US) 44718

( * ) Notice: Subject to any disclaimer, the term of this patent is extended or adjusted under 35 U.S.C. 154(b) by 332 days.

(21) Appl. No.: 09/974,491

(22) Filed: Oct. 10, 2001

(65) Prior Publication Data

US 2002/0138105 A1 Sep. 26, 2002

Related U.S. Application Data

(60) Provisional application No. 60/277,447, filed on Mar. 21, 2001.

(51) Int. Cl.
*A61N 1/375* (2006.01)
(52) U.S. Cl. .......................... 607/37; 607/10
(58) Field of Classification Search ................. 607/37, 607/36, 27, 115, 119, 122, 123, 148, 9, 10; 439/909
See application file for complete search history.

(56) References Cited

U.S. PATENT DOCUMENTS

| | | | | |
|---|---|---|---|---|
| 4,545,381 A | * | 10/1985 | Bournay et al. | 607/10 |
| 4,628,934 A | * | 12/1986 | Pohndorf et al. | 607/27 |
| 4,744,370 A | * | 5/1988 | Harris | 607/122 |
| 5,044,367 A | * | 9/1991 | Endres et al. | 607/4 |
| 5,306,292 A | * | 4/1994 | Lindegren | 607/11 |
| 5,405,375 A | * | 4/1995 | Ayers et al. | 607/122 |
| 5,423,873 A | * | 6/1995 | Neubauer et al. | 607/68 |
| 5,626,621 A | * | 5/1997 | Skoglund et al. | 607/10 |
| 5,782,892 A | * | 7/1998 | Castle et al. | 607/37 |
| 5,843,132 A | * | 12/1998 | Ilvento | 607/10 |
| 6,456,876 B1 | * | 9/2002 | Kroll | 607/4 |

OTHER PUBLICATIONS

Kass, David A., M.D., et al. *Improved Left Ventricular Mechanics from Acute VDD Pacing in Patients with Dilated Cardiomyopathy and Ventricular Conduction Delay; Circulation*, vol. 99, Mar. 1999.

Kerwin, W.F., et al. *Ventricular Contraction Abnormalities in Dilated Cardiomyopathy: Effect of Biventricular Pacing to Correct Interventricular Dyssynchrony; Journal of the American College of Cardiology.* vol. 2000. 35:1221-1227.

PSTC Paramedic Student Education—External Pacing; http://www.monroecc.edu/depts/pstc/paraspac.htm; Feb. 21, 2001.

External (Temporary) Pulse Generator; http://www.dantec.dk/brady/clinician/medtronicpacing/5388dc.html ; Jan. 10, 2002.

Model 5348 Specifications; http://www.dantec.dk/brady/clinician/medtronicpacing/clinspec.html; Feb. 21, 2001.

Model 5348 Disclosure; http://www.dantec.dk/brady/clinician/therapies/5348caut.html; Feb. 21, 2001.

Medtronic Hear Valves—Medtronic Temporary Pacing Leads; http://www.dantec.dk/cardiac/heartvalves/leads/6495.html; Feb. 21, 2001.

(Continued)

*Primary Examiner*—Kennedy Schaetzle
(74) *Attorney, Agent, or Firm*—Fish & Richardson P.C.

(57) ABSTRACT

Apparatus is disclosed for providing a practitioner the ability to switch from one cardiac pacing mode to another cardiac pacing mode when treating a patient suffering from heart failure due to discoordinate ventricular contraction. Also disclosed are methods of providing different modes of cardiac pacing to a cardiac pacing patient using the apparatus.

6 Claims, 8 Drawing Sheets

OTHER PUBLICATIONS

Entrez-PubMed: http://www..../query.fcgi?cmd=Retrieve&db=PubMed&list_ uids=1008953&dopt=Abstrac; Feb. 21, 2001.

Entrez-PubMed; http://www....query.fcgi?cmd=Retrieve&db=PubMed&list_uids=10987605&dopt=Abstrac; Feb. 21, 2001.

Continuing Education—Cardiac Pacemakers; http://www.nurseweek.com/ce/ce1104a.html; Feb. 21, 2001.

External (Temporary) Pulse Generator; http://www.medtronic.com/brady/clinician/medtronicpacing/5388spec.html; Feb. 21, 2001.

Pacemaker Talk: http://www.nurseweek.com/ce/pacetalk.html; Feb. 21, 2001.

Associated Press. Heart-failure Patients Are Given New Hope. New York Times May 30, 2000: A20 (col.5).

* cited by examiner

TEMPORARY BIVENTRICULAR PACING OF HEART AFTER HEART SURGERY

CROSS-REFERENCE TO RELATED APPLICATION

This application claims the benefit under Title 35, United States Code, §119(e)(1) of U.S. provisional application Ser. No. 60/277,447, filed Mar. 21, 2001.

TECHNICAL FIELD

This invention relates to therapeutic medical devices, and more particularly to cardiac pacing apparatus.

BACKGROUND

Patients with dilated cardiomyopathy occasionally undergo coronary artery bypass or valvular surgery. Heart failure, characterized by discoordinate ventricular contraction and non-uniform electrical activation, may be present temporarily following a myocardial infarction or a surgical insult. At the conclusion of an operative procedure when other modalities have failed to improve cardiac function, temporary cardiac pacing can be employed to improve hemodynamics.

For temporary cardiac pacing, fine gage insulated cardiac pacing leads are commonly attached to the cardiac patient's heart. One type of lead placement frequently done in conjunction with open-heart surgery is transthoracic lead placement. Such placement is normally performed when the patient is on full cardiopulmonary support after cardiac surgery. With transthoracic lead placement, positive and negative cardiac pacing leads are usually placed on the right ventricular epicardium, often by means of a surgical needle. If unipolar (single-conductor) leads are placed, they will be spaced apart from one another in order to include ventricular tissue within the intended electrical circuit. In cases in which a bipolar (dual-conductor) coaxial pacing lead is selected for use in cardiac pacing, only one lead will be placed, since such a lead contains two discrete electrodes, spaced apart for adequate electrical performance. The cardiac pacing lead(s) are then threaded through the skin and are cut. Commonly the leads will then be tested for adequate electrical threshold.

Equipment used to conduct temporary cardiac pacing in conjunction with internally implanted cardiac pacing leads includes an external pulse generator, also known as a temporary pulse generator, and a pacing cable. Temporary pulse generators are electronic devices packaged in the typical box-like enclosures, are generally powered by mercury (alkaline) batteries, and when in use are typically pinned to the patient's gown so the unit will not be dislodged when the patient shifts position, stands or sits. Examples of temporary pulse generators which have been used by practitioners include the Medtronic Single-Chamber Model 5348 External Pulse Generator, and the Medtronic Dual-Chamber Model 5388 External Pulse Generator. Temporary pulse generators provide controlled electrical pulses to the heart of a pacing patient which stimulate the heart to beat in concert with the pulses provided. Accordingly, such pulse generators will provide paired negative and positive terminals, which are integrated within an externally accessible connector port.

A pacing cable is used to connect the pulse generator with the pacing leads extending from the heart and through the skin of the patient. The pacing cable will have a connector to mate with above-mentioned connector port of the temporary pulse generator, and when the connector and the connector port are mated thereby, a positive lead in the pacing cable is electrically connected to the positive terminal of the connector port, and a negative lead in the pacing cable is electrically connected to the negative terminal of the connector port. The conductors within the cable will typically be made of copper, surrounded by flexible material to provide electrical insulation, flexibility, and toughness. Typically the positive and negative leads within the pacing cable will pass through the cable without branching, and will simply terminate at the other end of the cable in terminals designed to accept and connect to the fine gage cardiac pacing leads. One type of connection used is a clip connection, commonly called an 'alligator clip.' Another type of connection commonly used involves a threaded cylinder-type terminal, in which the pacing lead is inserted into an aperture in the cylinder, and the threaded portion of the terminal is screwed downward, securing the pacing lead within the terminal. Once the wiring is in place, temporary pacing can begin.

Traditionally, when cardiac patients have required post-operative temporary cardiac pacing, right ventricular pacing has been performed, in which cardiac pacing leads including a positive electrode and a negative electrode are attached to the right ventricle of the heart. Recently, however, practitioners have found certain patients will benefit when cardiac pacing is performed in concert upon on the right and left ventricle, and have responded by reconfiguring temporary pacing apparatus to provide 'biventricular pacing', i.e., a pacing regimen in which both the right and left ventricles are subjected to electrical pulses intended to stimulate simultaneous contraction. In such instances, a left negative cardiac pacing lead is placed on the left ventricular epicardium, generally equidistant from the septum (LAD) when compared to the right negative cardiac pacing lead, and the negative cardiac pacing leads are usually combined at the point they attach to the pacing cable (i.e., the alligator clip or threaded cylindrical terminal). Positive leads are usually similarly combined when biventricular pacing is provided.

Other practitioners have also recently found that some patients, such as those who suffer from left bundle branch block, may benefit when left ventricular pacing, as distinguished from right ventricular or biventricular pacing, can be provided after surgery. However, the temporary pulse generators and pacing cables which are commercially available are designed to provide pulse generation for single-site (generally the right ventricle) ventricular pacing, and will provide biventricular pacing only when cardiac pacing wires are doubled up at the terminal interfaces of the pacing cable. As a result, a practitioner concerned with providing his patients the fastest post-operative recovery possible will find presently available pacing apparatus incapable of providing him the flexibility to select from among the alternative modes of ventricular pacing described above in a quick fashion commensurate with efficient clinical care.

SUMMARY

Herein I have disclosed details of a pacing cable, which when used in conjunction with a cardiac temporary pulse generator, such as a Medtronic models 5348 and 5388, will provide temporary cardiac pacing. The pacing cable described in the present application allows for switching between multiple modes of ventricular pacing, including left ventricular, right ventricular, and biventricular pacing, and provides the capacity for the caregiver to switch between cardiac pacing modes easily in an effort to improve the clinical outcome.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
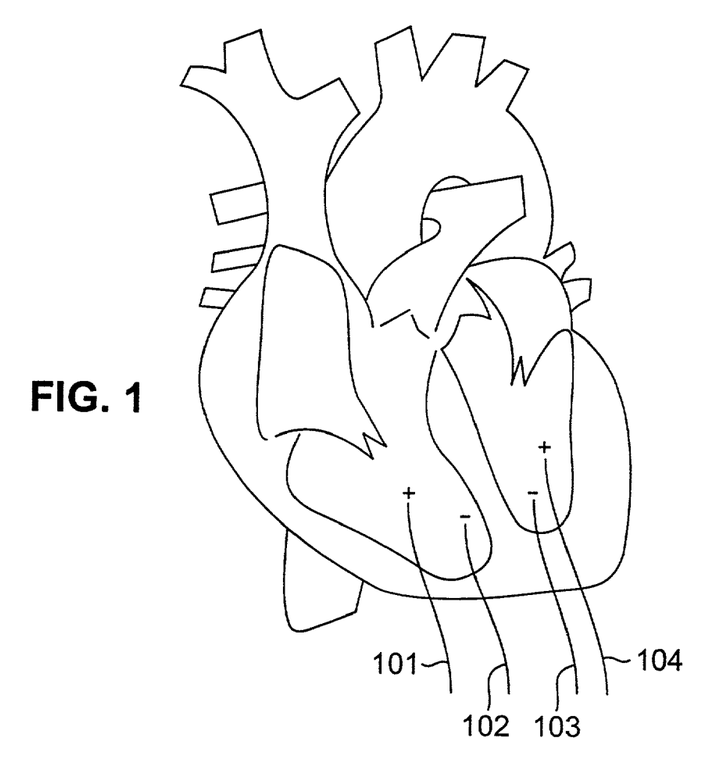
FIG. 1 shows four cardiac pacing leads placed in mechanical and electrical connection with a patient's heart at the time of surgery in accordance with the present application.
Figure 2:
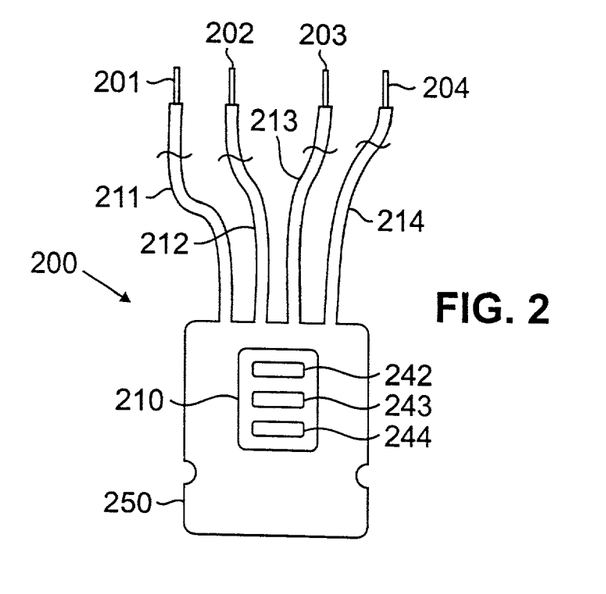
FIG. 2 shows a pacing cable in accordance with the present application.
Figure 3A:
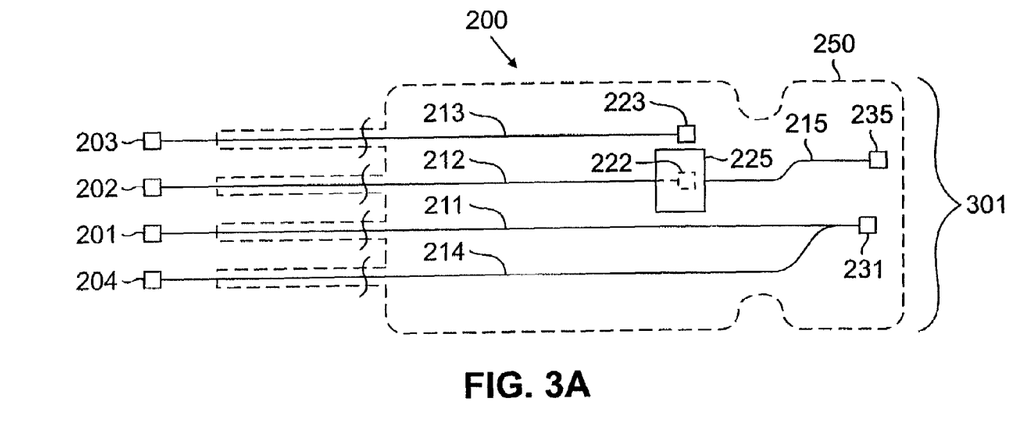
FIGS. 3A, 3B and 3C show wiring diagrams of pacing cables in accordance with the present application.
Figure 3B:
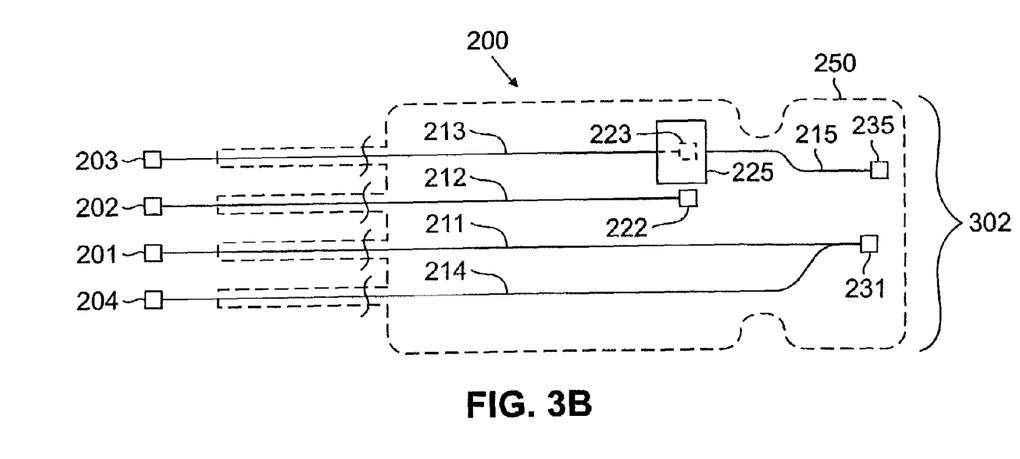
Figure 3C:
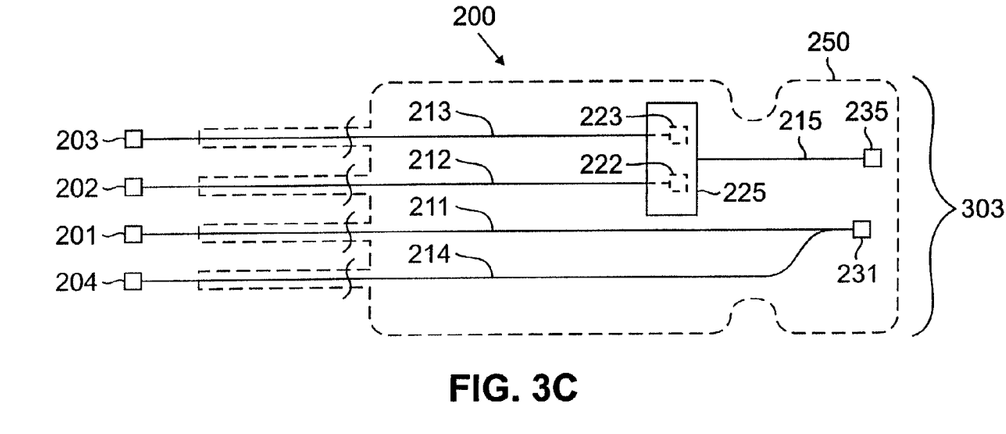

With regard to FIG. 1, transthoracic placement of four cardiac pacing leads is shown, two on the right ventricular epicardium, and two on the left ventricular epicardium. Lead 101 is the positive pacing lead for the right ventricle, and lead 102 is the negative pacing lead for the right ventricle. Lead 103 is the negative pacing lead for the left ventricle, and lead 104 is the positive pacing lead for the left ventricle. Pacing leads 101, 102, 103, and 104 are lead away from the heart and through the skin of the patient, in order to provide the conductive path necessary for temporary cardiac pacing.

The features of a pacing cable in accordance with the present application will be shown with reference to FIGS. 2, 3A, 3B, and 3C. Some terminals mentioned below are not visible in FIG. 2 because they are enclosed within the pacing cable 200, but all terminals are depicted, either by solid or dashed lines, in the pacing cable wiring diagrams 301, 302, and 303 shown in FIGS. 3A, 3B, and 3C respectively. The pacing leads 101, 102, 103 and 104 shown in FIG. 1 are attached, respectively, to terminals 201, 202, 203 and 204 of the pacing cable 200. Terminal 201 is at the end of positive lead 211, which passes directly through the pacing cable, ending at terminal 231 within the pulse generator connector 250. Terminal 204 is at the end of positive lead 214, which also passes directly through the pacing cable and ends at terminal 231 within the pulse generator connector. In this way a branched positive return lead is created within the pacing cable. Terminal 202 is at the end of negative lead 212, which passes through the cable, ending at terminal 222 within the cable. Terminal 203 is at the end of negative lead 213, which passes through the cable, ending at terminal 223 within the cable. Terminal 225 is within the cable at the end of negative lead 215, which passes through the cable, ending at terminal 235 within the pulse generator connector 250.

Toggle switch region 210 has three mode selection buttons 242, 243 and 244, which are adapted to be selectably manipulated so as to configure the pacing cable to provide the desired mode of pacing. Toggle switches are shown and were used in an embodiment, but any suitable switching mechanism known to those with skill in the art may be used for this purpose. As an example of the manner in which the toggle switch mechanism of FIG. 2 functions, the abstract wiring diagram 301 of FIG. 3A demonstrates that when mode selection button 242 is depressed, an electrical connection between terminals 222 and 225 is provided by terminal 225 being moved into contact with terminal 222, and that an electrical isolation of terminal 223 is provided at the same time, since terminal 225 has been moved away from it. Such an arrangement would permit right ventricular pacing. Alternatively, the abstract wiring diagram 302 of FIG. 3B demonstrates that when mode selection button 243 is depressed, an electrical connection between terminals 223 and 225 is provided by terminal 225 being moved into contact with terminal 223, and that an electrical isolation of terminal 222 is provided at the same time, since terminal 225 has been moved away from it. Such an arrangement would permit left ventricular pacing. Finally, the abstract wiring diagram 303 of FIG. 3C demonstrates that when modes selection button 244 is depressed, a simultaneous electrical connection between terminals 222, 223, and 225 is provided, resulting in a branched negative lead within the pacing cable, as shown in wiring diagram 303 of FIG. 3C. Such an arrangement would permit biventricular pacing.

Figure 4:
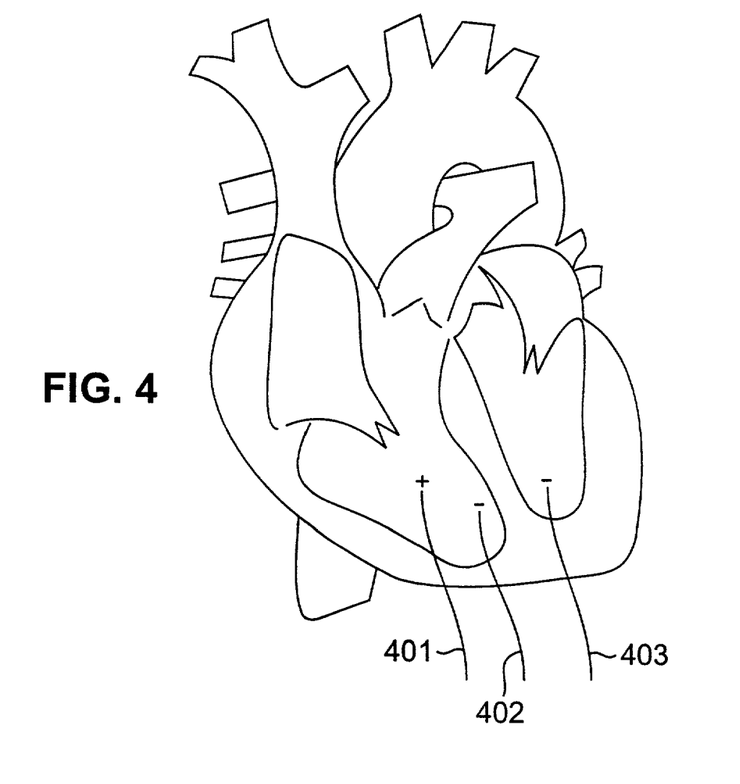
FIG. 4 shows three cardiac pacing leads placed in mechanical and electrical connection with a patient's heart at the time of surgery in accordance with the present application.
Figure 5:
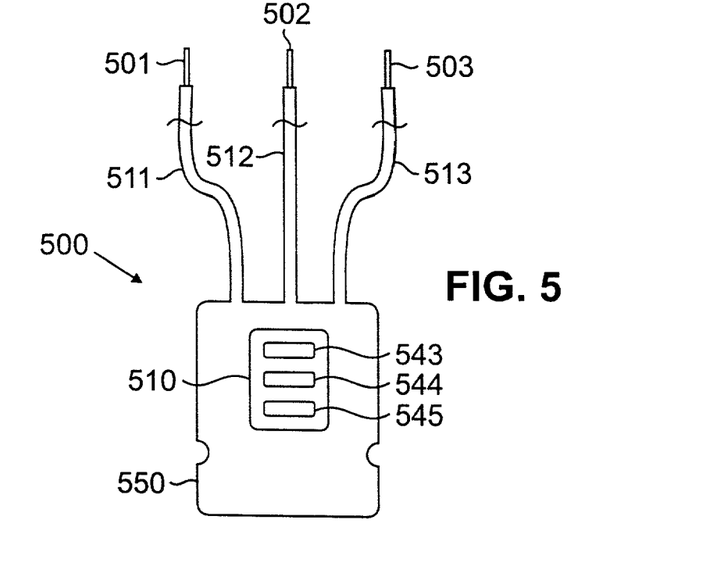
FIG. 5 shows a pacing cable in accordance with the present application.
Figure 6A:
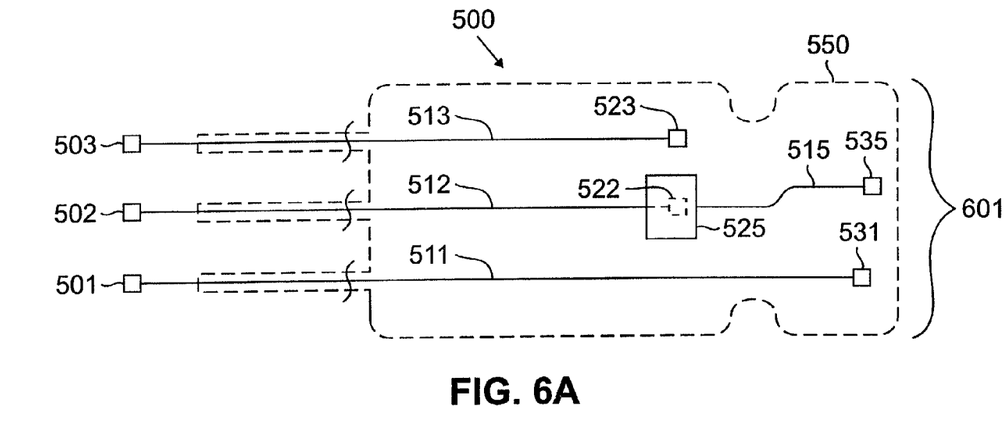
FIGS. 6A, 6B and 6C show wiring diagrams of pacing cables in accordance with the present application.
Figure 6B:
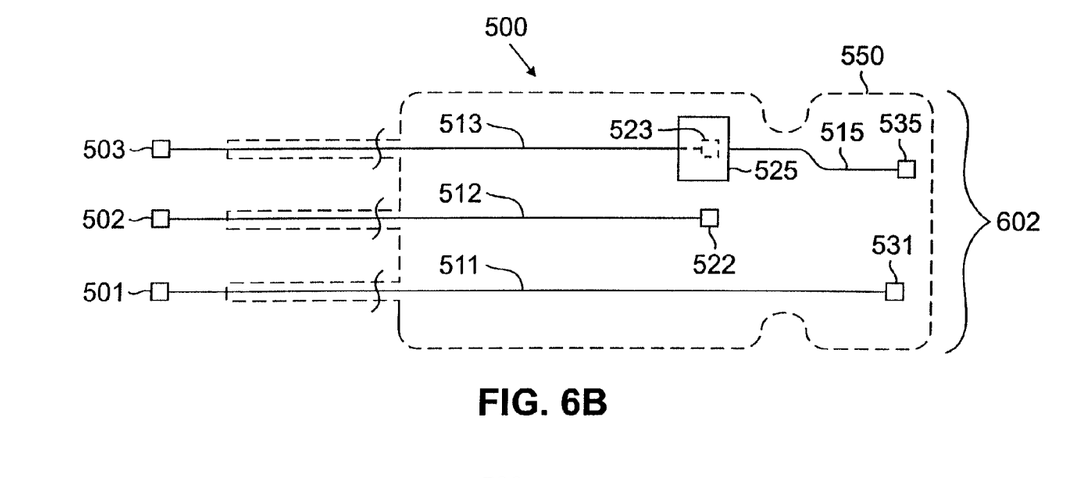
Figure 6C:
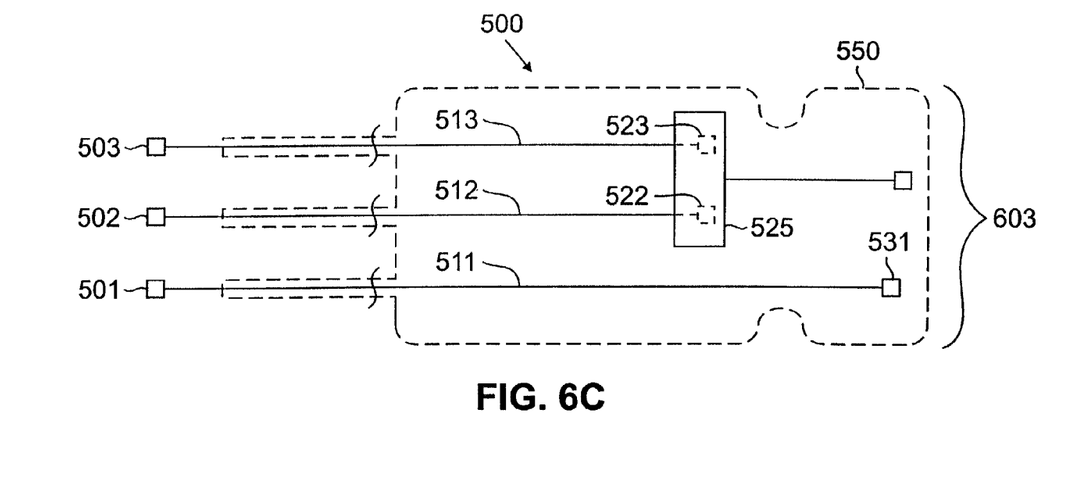

With regard to FIG. 4, transthoracic placement of three cardiac pacing leads is shown, two on the right ventricular epicardium, and one on the left ventricular epicardium. Lead 401 is a positive pacing lead, lead 402 is the negative pacing lead for the right ventricle, and lead 404 is the negative pacing lead for the left ventricle. Pacing leads 401, 402 and 403 are lead away from the heart and through the skin of the patient, in order to provide the conductive path necessary for temporary cardiac pacing. It has been observed that one positive pacing lead placed on the heart on either ventricle will provide an adequate return path for right ventricular, left ventricular, and biventricular pacing.

The features of another pacing cable in accordance with the present application will be shown with reference to FIGS. 5, 6A, 6B, and 6C. Some terminals mentioned below are not visible in FIG. 5 because they are enclosed within the pacing cable 500, but all terminals are depicted, either by solid or dashed lines, in the pacing cable wiring diagrams 601, 602, and 603 shown in FIGS. 6A, 6B, and 6C respectively. The pacing leads 401, 402 and 403 shown in FIG. 4 are attached, respectively, to terminals 501, 502 and 503 of the pacing cable 500. Terminal 501 is at the end of positive lead 511, which passes through the cable, ending at terminal 531 within the cable. Terminal 502 is at the end of negative lead 512, which passes through the cable, ending at terminal 522 within the cable. Terminal 503 is at the end of negative lead 513, which passes through the cable, ending at terminal 523 within the cable. Terminal 525 is within the cable at the end of negative lead 515, which passes through the cable, ending at terminal 535 within the pulse generator connector 550.

Toggle switch region 510 has three mode selection buttons 545, 543 and 544, which are adapted to be selectably manipulated so as to configure the pacing cable to provide the desired mode of pacing. Toggle switches are shown and were used in an embodiment, but any suitable switching mechanism known to those with skill in the art may be used for this purpose. As an example of the manner in which the toggle switch mechanism of FIG. 5 functions, the abstract wiring diagram 601 of FIG. 6A demonstrates that when mode selection button 642 is depressed, an electrical connection between terminals 522 and 525 is provided by terminal 525 being moved into contact with terminal 522, and that an electrical isolation of terminal 523 is provided at the same time, since terminal 525 has been moved away from it. Such an arrangement would permit right ventricular pacing. Alternatively, the abstract wiring diagram 602 of FIG. 6B demonstrates that when mode selection button 543 is depressed, an electrical connection between terminals 523 and 525 is provided by terminal 525 being moved into contact with terminal 523, and that an electrical isolation of terminal 522 is provided at the same time, since terminal 525 has been moved away from it. Such an arrangement would permit left ventricular pacing. Finally, the abstract wiring diagram 603 of FIG. 6C demonstrates that when modes selection button 544 is depressed, a simultaneous electrical connection between terminals 522, 523, and 525 is provided, resulting in a branched negative lead within the pacing cable, as shown in wiring diagram 603 of FIG. 6C. Such an arrangement would permit biventricular pacing.

Figure 7:
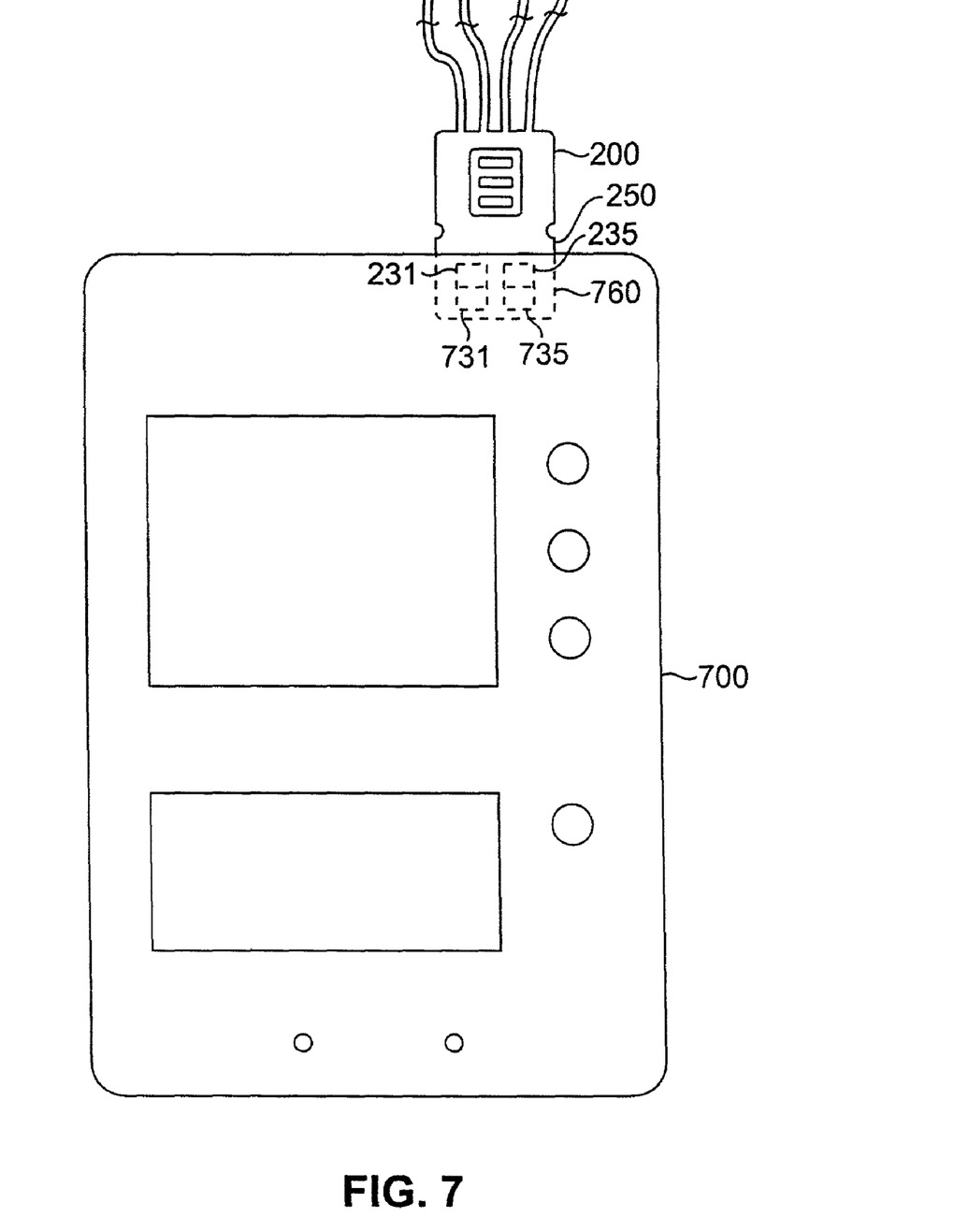
FIG. 7 shows a pacing cable in accordance with FIG. 2 and the present application connected to a standard temporary pulse generator.

As may be seen with reference to FIG. 7, pulse generator connector 250 of the pacing cable 200 may be connected to the connector port 760 at the ventricular position of a standard temporary pulse generator 700 such as the Medtronic model 5388. Positive terminal 231 connects with the positive terminal 731 of the connector port 760. Negative terminal 235 connects with the negative terminal 735 of the connector port 760. By means of selective operation of its mode selection feature as described above, the pacing cable 200 may be combined with a standard temporary pulse generator to provide three modes of cardiac pacing: right ventricular pacing (standard), left ventricular pacing, and biventricular pacing.

Figure 8:
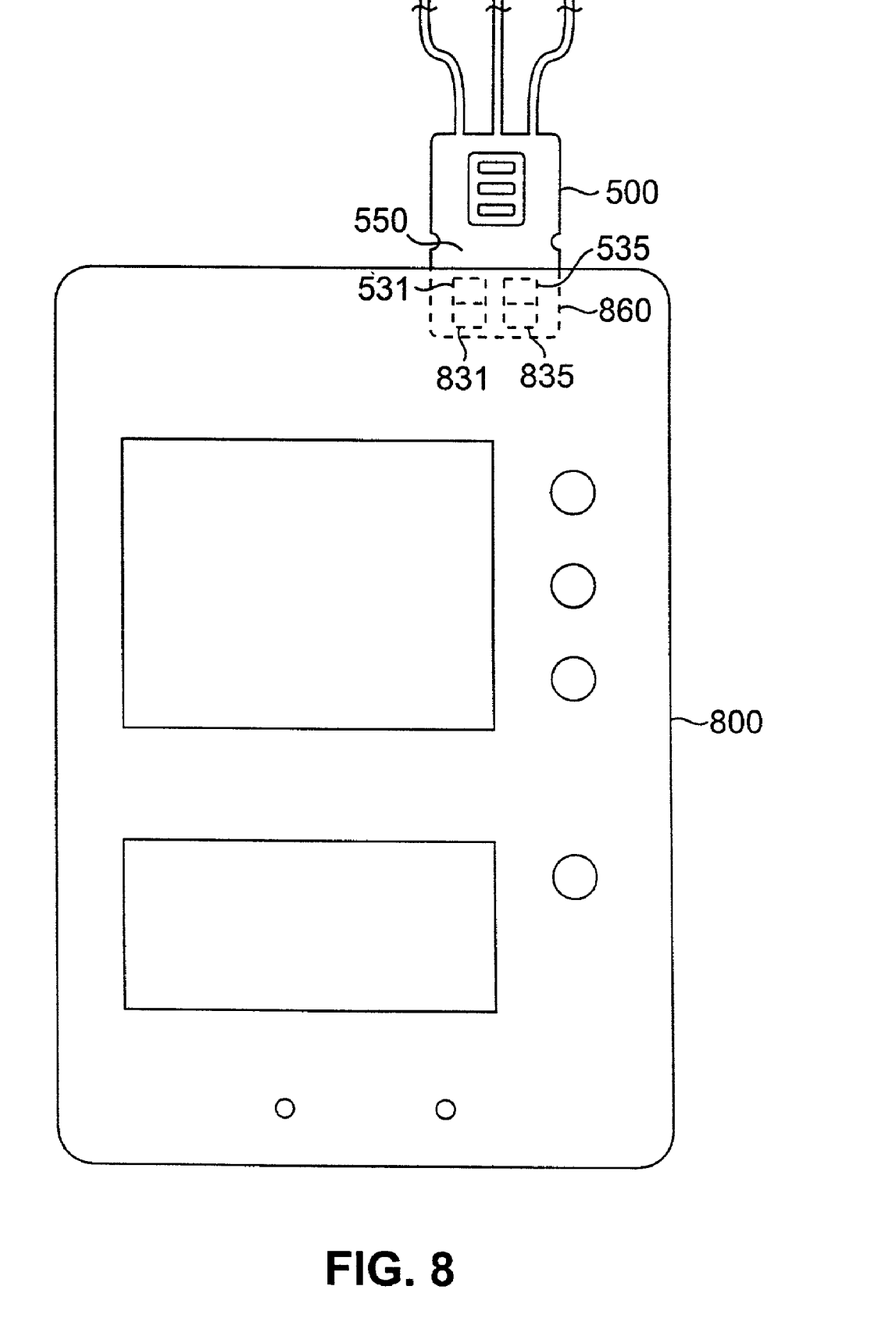
FIG. 8 shows a pacing cable in accordance with FIG. 5 and the present application connected to a standard temporary pulse generator.

As may be seen with reference to FIG. 8, pulse generator connector 550 of the pacing cable 500 may be connected to the connector port 860 at the ventricular position of a standard temporary pulse generator 800 such as the Medtronic model 5388. Positive terminal 531 connects with the positive terminal 831 of the connector port 860. Negative terminal 535 connects with the negative terminal 835 of the connector port 860. By means of selective operation of its mode selection feature as described above, the pacing cable 500 may be combined with a standard temporary pulse generator to provide three modes of cardiac pacing: right ventricular pacing (standard), left ventricular pacing, and biventricular pacing.

Figure 9:
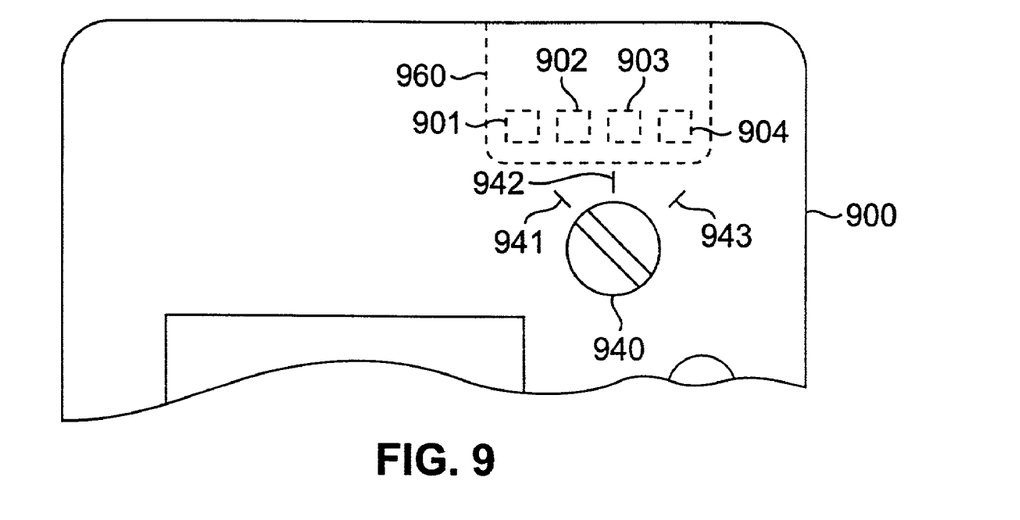
FIG. 9 shows a temporary pulse generator in accordance with the present application.

As may be seen with reference to FIG. 9, the switching function performed by pacing cable 200 in accordance with the present application may be incorporated within a temporary pulse generator itself. A temporary pulse generator 900 in accordance with the present application is shown in FIG. 9. The ventricular position has four terminals 901, 902, 903 and 904 within its connector port 960. These four terminals may be connected, respectively, to the pacing leads 101, 102, 103 and 104 of FIG. 1 by means of a simple, four lead pacing cable (not shown). Switch 940 at the ventricular position of the temporary pulse generator permits the practitioner to select between position 941, providing right ventricular pacing through terminals 901 and 902; position 942, providing left ventricular pacing through terminals 903 and 904; and position 943, providing biventricular pacing through all four terminals. A dial switch is shown in the embodiment, but any suitable switching mechanism known to those with skill in the art may be used for this purpose. Furthermore, any suitable arrangement of electronics and wiring within the temporary pulse generator may be employed by those with skill in the art to support the switching function shown.

Figure 10:
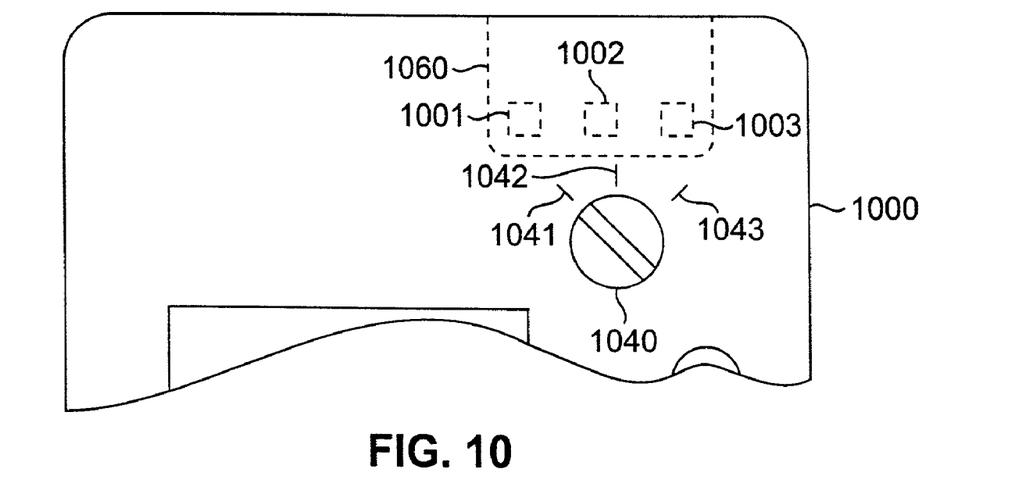
FIG. 10 shows a temporary pulse generator in accordance with the present application.

As may be seen with reference to FIG. 10, the switching function performed by pacing cable 500 in accordance with the present application may be incorporated within a temporary pulse generator itself. A temporary pulse generator 1000 in accordance with the present application is shown in FIG. 10. The ventricular position has three terminals 1001, 1002 and 1003 within its connector port 1060. These three terminals may be connected, respectively, to the pacing leads 401, 402 and 403 of FIG. 4 by means of a simple, three lead pacing cable (not shown). Switch 1040 at the ventricular position of the temporary pulse generator permits the practitioner to select between position 1041, providing right ventricular pacing through terminals 1001 and 1002; position 1042, providing left ventricular pacing through terminals 1001 and 1003; and position 1043, providing biventricular pacing through all three leads. A dial switch is shown in the embodiment, but any suitable switching mechanism known to those with skill in the art may be used for this purpose. Furthermore, any suitable arrangement of electronics and wiring within the temporary pulse generator may be employed by those with skill in the art to support the switching function shown.

It will be understood that various modifications may be made to the apparatus described in the present application without departing from the spirit and scope of the invention. For example, coaxial-type pacing leads may be used where the use of single-conductor pacing leads are described in the present application. Accordingly, other embodiments are within the scope of the following claims.

What is claimed is:

1. Cardiac pacing apparatus, comprising:
a temporary pulse generator having a first positive terminal and a first negative terminal within a first connector port, said first positive and first negative terminals being adapted to provide a cardiac pacing pulse suitable for single-mode cardiac pacing;
a pacing cable removably connectable to the first positive terminal and the first negative terminal of the temporary pulse generator to provide a selectable plurality of cardiac pacing operating modes, the pacing cable having a first, a second and a third conductor, a switching mechanism adapted to selectably activate said second and said third conductors, and a first connector connected to said temporary pulse generator at said first connector port, said pacing cable being adapted, by means of said switching mechanism, to provide ventricular pacing of a mode selected from the following group: left ventricular pacing through said first and said second conductor, right ventricular pacing through said first and said third conductor, and biventricular pacing through said first, said second, and said third conductor;
wherein said switching mechanism is accessible for hand manipulation by an operator while said first, second and third conductors are connected to a patient's heart; and
wherein said switching mechanism is adapted to selectably activate said second and said third conductors based on hand manipulation of the switching mechanism by the operator while said first, second and third conductors are connected to the patient's heart.

2. The cardiac pacing apparatus of claim 1
wherein said temporary pulse generator is adapted to be positioned outside of a patient's body; and
wherein said first, second and third conductors are electrically connected to the patient's heart for pulse delivery while said temporary pulse generator is positioned outside of the patient's body.

3. A cable for providing selectable alternative electrical connections between respective cardiac pacing leads and a pulse generator, comprising:
a housing;
first, second, and third cable leads having respective first, second, and third internal cable lead ends within the housing, the cable leads extending to respective first, second, and third external terminals, the first and second external terminals being adapted to achieve electrical continuity with respective cardiac pacing leads, and the third external terminal being adapted to achieve electrical continuity with a terminal of a pulse generator; and
a switch attached to the housing, the switch being adapted to selectably provide a continuity/isolation arrangement between the internal cable lead ends selected from the following set of continuity/isolation arrangements: the first internal cable lead end isolated and the second and third internal cable lead ends continuous, and the first and second and third internal cable lead ends continuous, said switch being further adapted to selectably provide the following continuity/isolation arrangement: the second internal cable lead end isolated and the first and third internal cable lead ends continuous;
wherein the switch includes a first button, adapted when actuated to isolate the first internal cable lead end and provide electrical continuity between the second and third internal cable lead ends, and a second button, adapted when actuated to isolate the second internal cable lead end and provide electrical continuity between the first and third internal cable lead ends, and third button, adapted when actuated to provide electrical continuity between the first and the second and the third internal cable lead ends.

4. The cable of claim 3 further comprising a fourth external terminal adapted to achieve electrical continuity with a terminal of a pulse generator, a fifth external terminal adapted to achieve electrical continuity with a cardiac pacing lead, and a fourth cable lead extending from the fourth external terminal, through the housing, to the fifth external terminal.

5. The cable of claim 4, the fourth external terminal being adapted to connect to two cable leads, and the cable further comprising a sixth external terminal adapted to achieve electrical continuity with a cardiac pacing lead, and a fifth cable lead extending from the fourth external terminal, through the housing, to the sixth external terminal.

6. The cable of claim 3 wherein the switch comprises a toggle switch.

* * * * *